(12) United States Patent
Blomqvist

(10) Patent No.: US 11,497,426 B2
(45) Date of Patent: Nov. 15, 2022

(54) APPARATUS AND ELECTRONIC CIRCUITRY FOR SENSING BIOSIGNALS

(71) Applicant: Nokia Technologies Oy, Espoo (FI)

(72) Inventor: Kim Blomqvist, Espoo (FI)

(73) Assignee: Nokia Technologies Oy, Espoo (FI)

( * ) Notice: Subject to any disclaimer, the term of this patent is extended or adjusted under 35 U.S.C. 154(b) by 372 days.

(21) Appl. No.: 16/648,752

(22) PCT Filed: Sep. 10, 2018

(86) PCT No.: PCT/FI2018/050637
§ 371 (c)(1),
(2) Date: Mar. 19, 2020

(87) PCT Pub. No.: WO2019/063874
PCT Pub. Date: Apr. 4, 2019

(65) Prior Publication Data
US 2020/0245884 A1 Aug. 6, 2020

(30) Foreign Application Priority Data
Sep. 26, 2017 (EP) .................................. 17193095

(51) Int. Cl.
*A61B 5/25* (2021.01)
*A61B 5/296* (2021.01)
(Continued)

(52) U.S. Cl.
CPC ................ *A61B 5/25* (2021.01); *A61B 5/277* (2021.01); *A61B 5/296* (2021.01); *A61B 5/0533* (2013.01);
(Continued)

(58) Field of Classification Search
CPC ............ A61B 5/25; A61B 5/296; A61B 5/277; A61B 2562/182
See application file for complete search history.

(56) References Cited

U.S. PATENT DOCUMENTS 8,781,562 B2 * 7/2014 Pekonen .................. A61B 5/30
600/509
9,445,740 B1 9/2016 Crone et al.
(Continued)

FOREIGN PATENT DOCUMENTS

CN 105027027 A 11/2015
CN 105310681 A 2/2016
(Continued)

OTHER PUBLICATIONS

Noh et al., "Ferroelectret film-based patch-type sensor for continuous blood pressure monitoring" Electronic Letters 2014.*
(Continued)

*Primary Examiner* — Tammara R Peyton
(74) *Attorney, Agent, or Firm* — Harrington & Smith

(57) ABSTRACT

An apparatus comprising: at least one electrode, having a first potential, arranged to sense a biosignal; a conductive shield provided over the at least one electrode where the conductive shield is configured to be driven to a second potential wherein the second potential is equivalent to the first potential plus a multiple of an inverted common mode voltage; and wherein the conductive shield is coupled to a drain to enable triboelectric charges to be dissipated.

18 Claims, 3 Drawing Sheets

(51) Int. Cl.
  *A61B 5/277* (2021.01)
  *A61B 5/0533* (2021.01)
  *A61B 5/291* (2021.01)
  *A61B 18/14* (2006.01)

(52) U.S. Cl.
  CPC ......... *A61B 5/291* (2021.01); *A61B 2018/147* (2013.01); *A61B 2562/0214* (2013.01); *A61B 2562/182* (2013.01)

(56) References Cited

U.S. PATENT DOCUMENTS

| | | | |
|---|---|---|---|
| 2012/0074961 | A1 | 3/2012 | Herrmann |
| 2015/0005585 | A1 | 1/2015 | Xu et al. |
| 2015/0042313 | A1 | 2/2015 | Kim et al. |
| 2016/0183834 | A1 | 6/2016 | Lee et al. |
| 2016/0256111 | A1 | 9/2016 | Cheng et al. |
| 2019/0099097 | A1 | 4/2019 | Blomqvist et al. |

FOREIGN PATENT DOCUMENTS

| | | |
|---|---|---|
| JP | 2015019837 A | 2/2015 |
| WO | 2008/152588 A2 | 12/2008 |
| WO | 2015/061282 A1 | 4/2015 |

OTHER PUBLICATIONS

Office action received for corresponding European Patent Application No. 17193095.1, dated May 29, 2020, 6 pages.
Office action received for corresponding European Patent Application No. 17193095.1, dated Oct. 15, 2020, 7 pages.
Office action received for corresponding European Patent Application No. 17193095.1, dated Dec. 1, 2021, 5 pages.
Office action received for corresponding Chinese Patent Application No. 201880062144.6, dated Apr. 14, 2022, 9 pages of office action and no page of translation available.
Office action received for corresponding European Patent Application No. 17193095.1, dated May 6, 2021, 4 pages.
Office action received for corresponding Indian Patent Application No. 202047017546, dated May 31, 2021, 7 pages.
Lim et al., "Capacitive Driven-right-leg Grounding in Indirect-contact ECG Measurement", Annual International Conference of the IEEE Engineering in Medicine and Biology, Aug. 31-Sep. 4, 2010, pp. 1250-1253.
Peng et al., "Non-contact, Capacitive Biosensor Electrodes for Electrostatic Charge Reduction", Sensors, Nov. 3-6, 2013, 4 pages.
Lim et al., "Capacitive Measurement of ECG for Ubiquitous Healthcare", Annals of Biomedical Engineering, vol. 42, No. 11, Nov. 2014, pp. 2218-2227.
Wartzek et al., "Triboelectricity in Capacitive Biopotential Measurements", IEEE Transactions on Biomedical Engineering, vol. 58, No. 5, May 2011, pp. 1268-1277.
Extended European Search Report received for corresponding European Patent Application No. 17193095.1, dated Jan. 8, 2018, 11 pages.
International Search Report and Written Opinion received for corresponding Patent Cooperation Treaty Application No. PCT/FI2018/050637, dated Oct. 23, 2018, 14 pages.

* cited by examiner

APPARATUS AND ELECTRONIC CIRCUITRY FOR SENSING BIOSIGNALS

RELATED APPLICATION

This application claims priority to PCT Application No. PCT/FI2018/050637, filed on Sep. 10, 2018, which claims priority to EP Application No. 17193095.1, filed on Sep. 26, 2017, each of which is incorporated herein by reference in its entirety.

TECHNOLOGICAL FIELD

Examples of the disclosure relate to apparatus for sensing biosignals. In particular they relate to apparatus for sensing a biosignal where the apparatus is arranged to reduce the noise in the output signal.

BACKGROUND

Apparatus for sensing biosignals typically comprise electrodes which can be coupled to a subject's body to detect the biosignals. The subject could be a person or an animal. The biosignals may provide information indicative about the health or state of the subject. It is useful to provide an apparatus for sensing biosignals which provides a good quality output signal.

BRIEF SUMMARY

According to various, but not necessarily all, examples of the disclosure there is provided an apparatus comprising: at least one electrode, having a first potential, suitable for sensing a biosignal; a conductive shield provided over the at least one electrode where the conductive shield is configured to be driven to a second potential wherein the second potential is equivalent to the first potential plus a component derived from an inverted common mode voltage, wherein the common mode voltage originates from the biosignal; and wherein the conductive shield is coupled to a drain to enable triboelectric charges to be dissipated.

The common mode voltage may is an average voltage between the at least one electrode and another electrode arranged to sense the biosignal.

The conductive shield may be arranged to contact a user when the apparatus is in use.

The apparatus may comprise electronic circuitry arranged to drive the conductive shield using the inverted common mode voltage. The electronic circuitry may comprise an amplifier having a low output impedance arranged to drive the conductive shield. The amplifier having a low output impedance may act as the drain to enable triboelectric charges to be dissipated.

The conductive shield may comprise one or more discontinuities.

The conductive shield may be provided over the electrode so that in use the conductive shield is positioned between the user and the electrode.

The conductive shield may be provided in the same layer as the electrode.

The conductive shield and the electrode may be provided in an interdigitated structure.

The apparatus may comprise a plurality of electrodes and a plurality of conductive shields over the electrodes wherein each of the conductive shields are driven to a potential equivalent to the potential of the corresponding electrode plus a component derived from an inverted common mode voltage, wherein the common mode signal originates from the biosignal.

The component derived from the inverted common mode voltage may be a multiple of the inverted common mode voltage. The multiple of the inverted common mode voltage may be 1.

The apparatus may comprise circuitry arranged to provide different input signals to the different conductive shields so that different conductive shields are driven to different potentials.

A first electrode may be arranged to be coupled to a first part of a user's body and a second electrode may be arranged to be coupled to a second part of a user's body.

The electrodes may be capacitive electrodes arranged to detect bioelectric signals. The apparatus may comprise a conductive guard associated with the capacitive electrode wherein the conductive guard is positioned relative to the electrode to protect the electrode from the environment. The conductive guard may be driven to the same potential as the capacitive electrode. The bioelectrical signal may comprise at least one of electrocardiogram signal, electroencephalogram signal, electromyogram signal, electrooculogram signal, galvanic skin potential.

According to various, but not necessarily all, embodiments of the invention there is provided examples as claimed in the appended claims.

BRIEF DESCRIPTION

For a better understanding of various examples that are useful for understanding the detailed description, reference will now be made by way of example only to the accompanying drawings in which.

DETAILED DESCRIPTION

Figure 1:
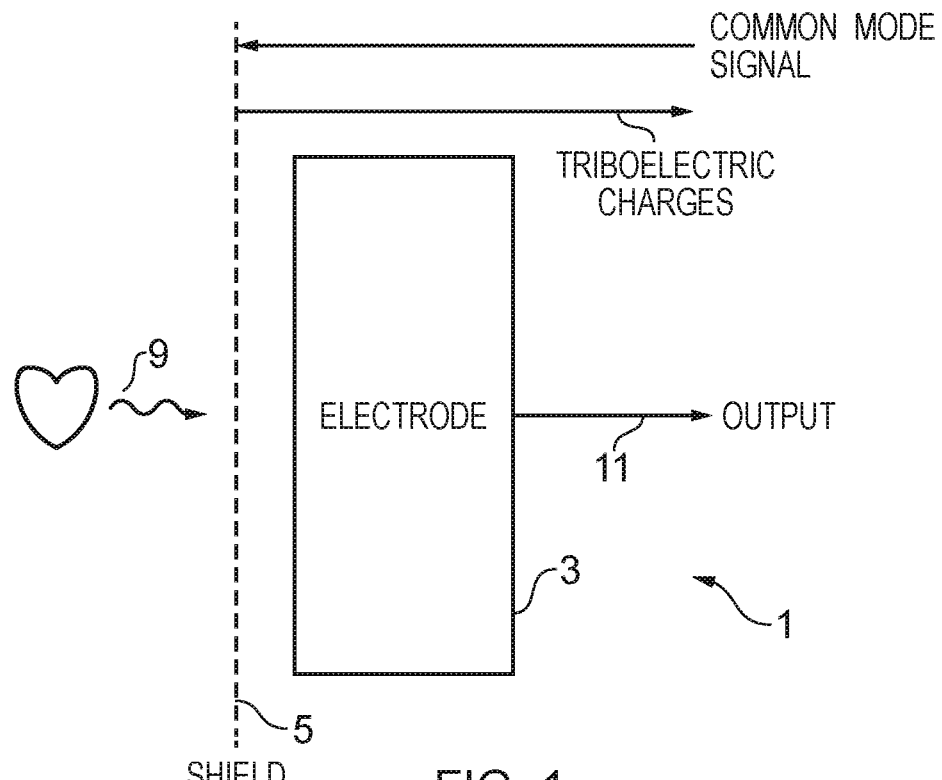
FIG. 1 illustrates an apparatus.

The figures show apparatus 1 which may be arranged to sense biosignals. The example apparatus 1 comprise at least one electrode 3 and a conductive shield 5. The at least one electrode 1 may be arranged to sense a biosignal 9 and the conductive shield 5 may be arranged to reduce the noise in the output signal 11 provided by the at least one electrode 3.

FIG. 1 schematically illustrates an apparatus 1 according to examples of the disclosure. The apparatus 1 may be for sensing biosignals 9. The apparatus 1 comprises at least one electrode 3, having a first potential, suitable for sensing a biosignal 9; a conductive shield 5 provided over the at least one electrode 3 where the conductive shield 5 is configured to be driven to a second potential, wherein the second potential is equivalent to the first potential plus a component derived from an inverted common mode voltage, wherein the common mode voltage originates from the biosignal; and wherein the conductive shield 5 is coupled to a drain to enable triboelectric charges to be dissipated.

The biosignal 9 that is sensed by the apparatus 1 could be any signal that is generated by a user's body. In some examples the biosignal 9 may comprise an autonomic signal which may be controlled subconsciously by the user. The biosignal 9 may comprise signals which are generated by autonomic bodily functions such as the user's heartbeat. In some examples the biosignal 9 could comprise a bioelectrical signal such as a biopotential signal. The bioelectrical signal could comprise at least one of electrocardiogram signal, electroencephalogram signal, electromyogram signal, electrooculogram signal, galvanic skin potential or any other suitable type of bioelectrical signal.

The apparatus 1 is arranged to be positioned on the body of a user so as to enable the biosignal 9 to be sensed. In some examples of the disclosure the apparatus 1 may be provided within a small wearable pad, or other device, which may be arranged to be attached to the user's body so that the apparatus 1 can detect biosignals 9 generated by the user's body. The apparatus 1 may be arranged to be adhered or otherwise secured to the user's body. This may enable the user to move but ensure that the apparatus 1 remains fixed in position on the user's body. The apparatus 1 may be arranged to be positioned on any suitable part of the user's body, such as the torso, limbs, head or any other location. In some examples the apparatus 1 may be arranged to be adhered to the user's clothing so that the biosignal 9 can be detected through the fabric of the clothing.

The electrode 3 comprises means which may be arranged to sense the biosignal 9 and provide an output signal 11 indicative of the detected biosignal 9. The electrode 3 may be made of any suitable conductive material such as copper. The electrode 3 could be a capacitive coupling electrode which may be arranged to detect charge displacements caused by bioelectric signals within the user's body. In such examples the apparatus 1 may be arranged so that an insulating material is provided between the electrode 3 and the user's body.

The electrode 3 has a first potential. The first potential may be dependent upon the biosignals 9 so that the potential of the electrode 3 is time varying.

The electrode 3 may be coupled to the conductive shield 5. In some examples the electrode 3 may be coupled to the conductive shield 5 via an insulating material or any other suitable means. In examples of the disclosure the conductive shield 5 may be provided over the electrode 3. The conductive shield 5 may overlay the electrode 3 so that the conductive shield 5 extends over the entire of the surface of the electrode 3.

The conductive shield 5 may comprise any suitable conductive material such as copper.

The conductive shield 5 may comprise one or more discontinuities within the surface of the conductive shield 5. The discontinuities may provide gaps within the conductive material so as to enable the electrode 3 to capacitively sense bioelectric signals through the conductive shield 5. In some examples a nonconductive material may be provided within the discontinuities. In other examples the discontinuities may provide gaps in the surface of the conductive shield 5.

In some examples the conductive shield 5 may be arranged to contact a user when the apparatus 1 is in use. This may provide a direct current path to be provided between the user and the conductive shield 5. This may enable triboelectric charges to be transferred from the user to the conductive shield 5. The conductive shield 5 may be connected to a drain to enable the triboelectric charges to be dissipated from the conductive shield 5. The conductive shield 5 therefore provides means for shielding the electrode 3 from triboelectric charges.

Figure 3A:
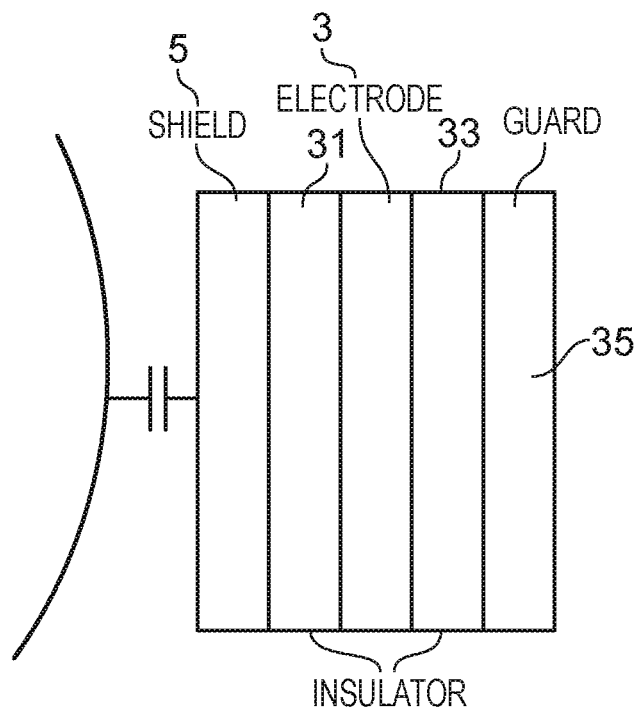
FIGS. 3A to 3E illustrate an apparatus and components of an apparatus.

In some examples the conductive shield 5 may be positioned within the apparatus 1 so that in use the conductive shield 5 is positioned between the user and the electrode 3, see for example FIG. 3A. In other examples the conductive shield 5 may be positioned within the apparatus 1 so that the conductive shield 5 interleaves the electrode 3, see for examples, FIGS. 4A and 4B. In such examples the electrode 3 and conductive shield 5 may be provided within the same layer of the apparatus 1.

The conductive shield 5 is driven to a second potential so as to reduce the noise in the output signal 11 provided by the electrode 3. The second potential is equivalent to the first potential of the electrode 3 plus a component derived from an inverted common mode voltage. The common mode voltage may originate from the biosignal.

The common mode voltage is an average voltage between the electrode 3 and another electrode arranged to sense a biosignal 9. The another electrode may be a further electrode within the same sensing apparatus 1. The another electrode may be arranged to sense biosignals 9 in the same manner as the electrode 3. The another electrode may be coupled to another part of the user so that the electrodes are arranged to sense the biosignals 9 from different parts of the user's body. For example a first electrode could be positioned to detect biosignals from a user's right arm while another electrode could be positioned to detect biosignals from the user's left arm.

Where the apparatus comprises two electrodes the common mode voltage may be the half sum voltage. Where the sensing apparatus 1 comprises a plurality of another electrodes the average voltage may be the mean voltage.

The component derived from the inverted common mode voltage may comprise a multiple of the inverted common mode voltage. Any suitable multiple of the inverted common mode voltage may be used in examples of the disclosure. In some examples the multiple could be 1. In other examples the multiple could be 10, 100, 1000 or any other suitable multiple.

The conductive shield 5 is coupled to electronic circuitry which may be arranged to drive the conductive shield using a component derived from the inverted common mode voltage. Examples of electronic circuitry which may be used in some examples of the disclosure are shown in FIG. 2.

In the example of FIG. 1 only one electrode 3 and one conductive shield 5 is shown. In other examples the apparatus 1 may comprise a plurality of electrodes 3 and a plurality of conductive shields 5. FIG. 2 illustrates an apparatus 1 comprising a plurality of electrodes 3 and a plurality of conductive shields 5 and electronic circuitry 21 arranged to control the potential of the conductive shield 5.

Figure 2:
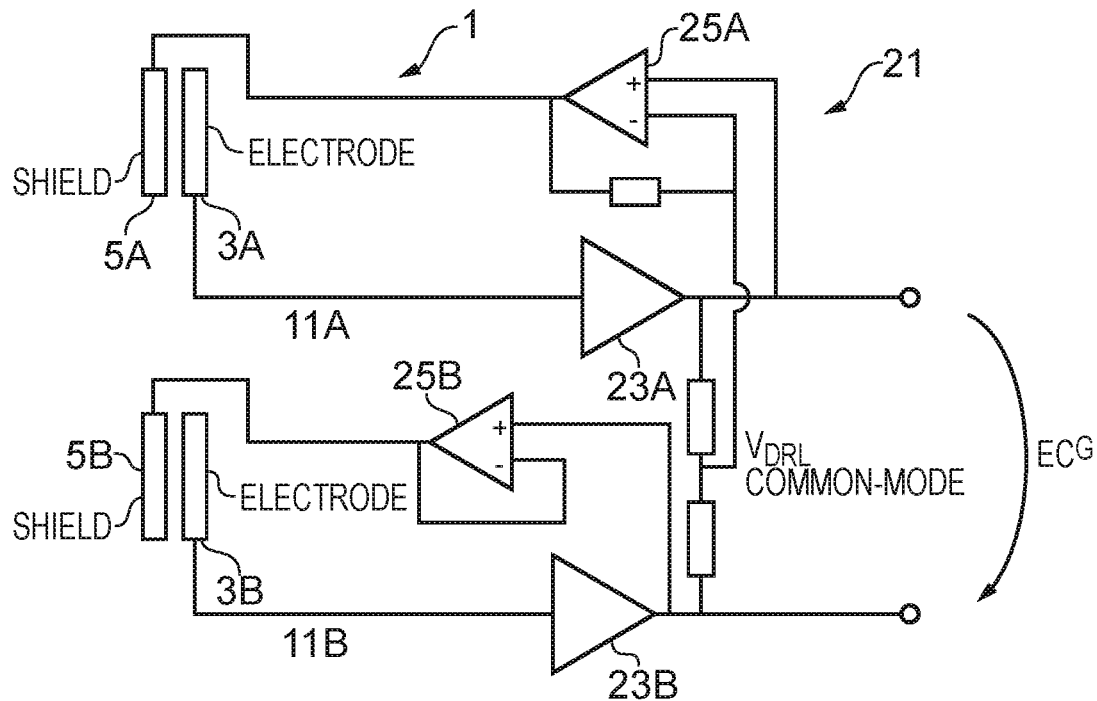
FIG. 2 illustrates an apparatus comprising electronic circuitry.

The example apparatus 1 of FIG. 2 comprises a first electrode 3A, a second electrode 3B, a first conductive shield 5A and a second conductive shield 5B. The first conductive shield 5A is associated with the first electrode 3A and the second conductive shield 5B is associated with the second electrode 3B.

The electrodes 3A, 3B may comprise conductive material arranged to detect bioelectrical signals 9 as described above. The conductive shields 5A, 5B may comprise conductive structures arranged as described above.

The electronic circuitry 21 shown in FIG. 2 comprises means for controlling the common mode potential of the first conductive shield 5A. It is to be appreciated that the apparatus 1 may also comprise electronic circuitry arranged to control the common mode potential of the second conductive shield 5B or other conductive shields within the apparatus 1.

In the example of FIG. 2 the output 11A of the first electrode 3A is provided to a first non-inverting amplifier 23A and the output 11B of the second electrode 3B is provided to a second non inverting amplifier 23B. In the example of FIG. 2 the outputs from the first and second electrodes 3A, 3B provide an electrocardiogram (ECG) signal. In such examples the apparatus 1 is arranged so that the first and second electrodes 3A, 3B can be positioned on appropriate parts of a user's body. For example the first electrode 3A could be provided on a user's right arm while the second electrode 3B could be provided the user's left arm. It is to be appreciated that the apparatus 1 could also comprise further electrodes which may be positioned in other locations around the rest of the user's body so as to enable the rest of the ECG data to be obtained. For instance the apparatus 1 could comprise other sensing electrodes 3 which may be positioned across the user's chest and on the user's legs.

The first conductive shield 5A is coupled to circuitry 21 which is arranged to use an inverting amplifier to drive the first conductive shield 5A to a potential which is equivalent to the potential of the first electrode 3 plus the inverted common mode potential. In the example of FIG. 2 the circuitry 21 comprises an inverting amplifier 25A. The output of the first non-inverting amplifier 23A is provided to the positive terminal of the inverting amplifier 25A. The common mode potential at the first electrode 3A and the second electrode 3B is provided to the negative terminal of the inverting amplifier 25A. This drives the first conductive shield 5A to a second potential which is equivalent to the potential of the first electrode 3 plus the inverted common mode potential.

In the example of FIG. 2 the inverting amplifier 25A has a gain of −1. In this example the multiple of the inverted common mode voltage is 1. In other examples the inverting amplifier 25A could have a different gain. For example, the gain could be −10, −100, −1000 or any other suitable gain. In such cases the multiple of the inverted common mode voltage would be 10, 100 or 1000.

The inverting amplifier 25A has a low output impedance. The low output impedance acts as a drain to enable triboelectric charges that are transferred to the first conductive shield 5A to be dissipated. This enables the same conductive shield 5A to be used to reduce the noise in the output signals and also to dissipate triboelectric charges. This may reduce the total number of components needed within the apparatus 1.

The output impedance of the inverting amplifier 25A may be low compared to the input impedance of the non-inverting amplifier 23A. The output impedance of the inverting amplifier 25A must be sufficiently low so as to limit the current that could be driven to the user, in the event of failure of any part of the circuitry 21, to a safe amount. For instance, where the electrodes 3A, 3B are arranged to provide an ECG signal the output impedance of the inverting amplifier 25A must be significantly lower than the input impedance of the non-inverting amplifier 23A. For example, the output impedance of the inverting amplifier 25A could be several orders of magnitude lower than the input impedance of the non-inverting amplifier 23A. In some cases the output impedance of the inverting amplifier 25A could be at least four orders of magnitude lower than the input impedance of the non-inverting amplifier 23A. In such cases the output impedance of the inverting amplifier 25A could be of the order of 1 Mohm while the input resistance of the non-inverting amplifier 23A could be of the order or tens of gigaohms or even a teraohm. In other cases the output impedance of the inverting amplifier 25A could be even lower, for example the output impedance could be around 50-100 Kohm. In some cases the output impedance of the inverting amplifier 25A could be arranged to provide a time constant that is at least five times lower than the time constant for the non-inverting amplifier 23A.

The electronic circuitry 21 also comprises a second inverting amplifier 25B which is arranged so that the output 11B of the second electrode 3B is provided to the positive terminal of the second inverting amplifier 25B and the output of the second inverting amplifier 25B is coupled to the second conductive shield 5B. This controls the potential of second conductive shield 5B.

In the example apparatus 1 of FIG. 2 only the first conductive shield 5A is driven to the second potential given by the first potential plus the multiple of the inverted common noise potential. It is to be appreciated that in other examples the second conductive shield 5B could also be driven to a potential which is equivalent to the sum of the potential of the corresponding electrode 3B plus a component derived from a common mode voltage. It is to be appreciated that the first conductive shield 5A and the second conductive shield 5B would be driven to different potentials because they are associated with different electrodes 3A, 3B which may have different potentials. Each of the conductive shields 5A, 5B would be coupled to circuitry arranged to drive the conductive shields 5A, 5B to the appropriate voltage.

In the illustrative example apparatus 1 of FIG. 2 only two electrodes 3A, 3B and corresponding conductive shields 5A, 5B are shown. It is to be appreciated that in other examples of the disclosure any number of electrodes 3 and corresponding conductive shields 5 could be provided. In some examples each of the conductive shields 5 may be driven, using an inverted common mode potential, to a potential equivalent to the potential of the corresponding electrode 3 plus a component derived from an inverted common mode potential. In other examples only a subset of the conductive shields 5 might be driven to such a potential. The electronic circuitry 21 of the apparatus 1 is arranged to provide different input signals to the different conductive shields 5 so that different conductive shields 5 are driven to different potentials. The different potentials may have different values as determined by the different input signals.

Where the apparatus 1 comprises a plurality of sensing electrodes 3 and conductive shields 5 each of the sensing electrodes 3 within the apparatus may be coupled to a corresponding conductive shield 5. In such examples the number of sensing electrodes 3 within the apparatus 1 may be equal to the number of conductive shields 5. The different electrodes 3 could be arranged to detect the same biosignal 9 at different locations on the user's body. Each of the sensing electrodes 3 may be arranged to detect a biosignal independently of the other sensing electrodes 3 within the apparatus 1.

FIGS. 3A to 3E illustrate an example apparatus 1 and components of the example apparatus 1. FIGS. 3A to 3E show only the sensing components of the apparatus 1. It is to be appreciated that the apparatus 1 may also comprise electronic circuitry 21 which may be arranged as described above.

Figure 3B:
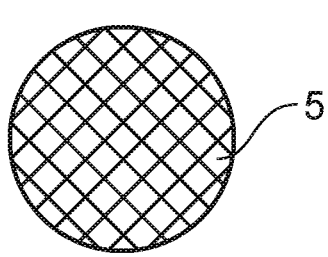
Figure 3D:
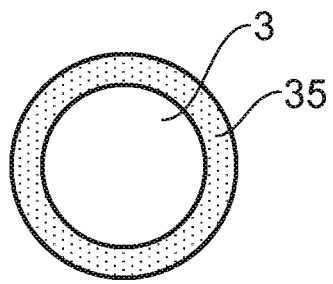
Figure 3C:
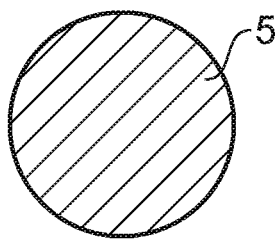
Figure 3E:
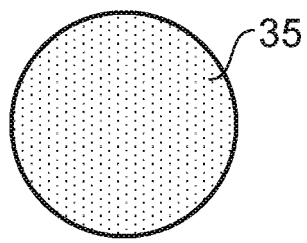

FIG. 3A shows a cross section of the apparatus 1, FIG. 3B shows a plan view of a conductive shield 5, FIG. 3C shows a plan view of an alternative conductive shield 5, FIG. 3D shows a plan view of an electrode 3 and FIG. 3E shows a plan view of a conductive guard.

As shown in the cross section of FIG. 3A the apparatus 1 comprises a conductive shield 5, a first insulating layer 31, an electrode 3, a second insulating layer 33 and a conductive guard 35.

The conductive shield 5 is provided as the upper layer of the apparatus 1. The conductive shield 5 is positioned within the apparatus 1 so that in use the conductive shield 5 may be positioned adjacent to the user's body. In some examples the conductive shield 5 may provide the outer surface of the apparatus 1 so that the conductive shield 5 directly touches the user when the apparatus 1 is in use. In other examples the conductive shield 5 could be coated with an insulating material. The insulating material could comprise any suitable material. In some examples the insulating material may comprise a fabric. The fabric could comprise a material which, like human skin, has a tendency to charge positively such as nylon. In some examples the material could comprise a material which has a tendency to hold water molecules from the surrounding environment such as nylon. In other examples the insulating material could comprise a solder mask.

The conductive shield 5 may be arranged to enable direct charge transfer between the user and the conductive shield 5. This may enable triboelectric charges to be dissipated by the conductive shield 5 to reduce the effect of the triboelectric charges on the electrode 3 and the output signal 11 provided by the electrode 3.

FIGS. 3B and 3C show plan views of conductive shields 5 which could be used in examples of the disclosure. In both FIGS. 3B and 3C the conductive shields have a circular shape. It is to be appreciated that other shapes could be used for the conductive shield 5 in other examples of the disclosure.

In the FIG. 3B the conductive shield 5 comprises a grid structure. The grid structure comprises a plurality of orthogonal members that are arranged to intersect each other. The intersections create discontinuities in the surface of the conductive shield 5.

In FIG. 3C the conductive shield 5 comprises a comb structure. The comb structure comprises a plurality of parallel members that extend across the surface of the conductive shield 5. A plurality of discontinuities are provided between the parallel members of the comb structure. The comb structure of FIG. 3C could be used as an alternative to the grid structure of FIG. 3C. It is to be appreciated that other structures and patterns could be used in other examples of the disclosure.

The first insulating layer 31 is positioned beneath the conductive shield 5. The first insulating layer 31 may comprise a thin film of any suitable insulating material. The first insulating material may comprise any material that prevents direct charge transfer between the conductive shield 5 and the electrode 3. The first insulating layer 31 may ensure that there is no galvanic connection between the conductive shield 5 and the electrode 3. This may enable the electrode 3 to act as a capacitive coupling electrode to sense the biosignals 9.

The electrode 3 is positioned beneath the first insulating layer 31. The first insulating layer 31 may couple the electrode 3 to the conductive shield 5. The electrode 3 may be any means for sensing the biosignal 9 which may be as described above.

FIG. 3D shows an example plan view of the electrode 3. In the example of FIG. 3D the electrode 3 has the same shape as the conductive shield 5 so the electrode 3 also has a circular shape. However the electrode 3 may be smaller than the conductive shield 5 and the conductive guard 35 so that the conductive shield 5 and the conductive guard 35 extend beyond the edge of the electrode 3. In the plan view of the electrode 3 the conductive guard 35 can be seen underneath the electrode 3.

The second insulating layer 33 is positioned beneath the electrode 3. The second insulating layer 33 may comprise a thin film of any suitable insulating material. The insulating material may comprise any material that prevents direct charge transfer between the electrode 3 and the conductive guard 35. The second insulating layer 33 may ensure that there is no galvanic connection between the electrode 3 and the conductive guard 35.

The conductive guard 35 comprises a conductive layer which may be arranged to protect the electrode 3 from the electronic circuitry 21 and other environmental factors. The conductive guard 35 may comprises a continuous conductive layer with no discontinuities. The conductive guard 35 may be coupled to the electronic circuitry 21. The electronic circuitry may be arranged to drive the conductive guard 35 to the same potential as the electrode 3.

FIG. 3E shows a plan view of an example guard 35. In the example of FIG. 3E the conductive guard 35 has the same shape as the conductive shield 5 and the electrode 3 so the conductive guard 35 also has a circular shape. The conductive guard 35 may be larger than the electrode 3 so that the conductive guard 35 extends beyond the edge of the electrode 3.

Figure 4A:
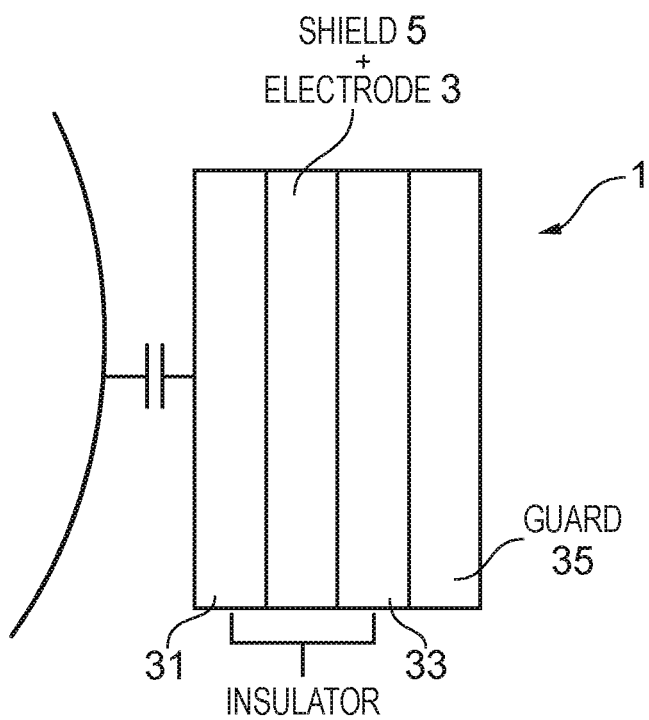
FIGS. 4A and 4B illustrate another apparatus and components of the apparatus.
Figure 4B:
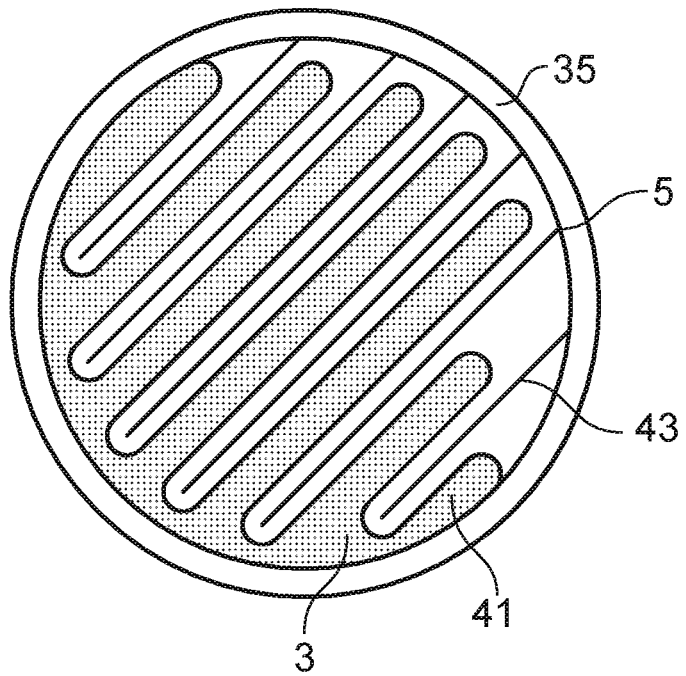

FIGS. 4A and 4B illustrate another example apparatus 1 and components of the example apparatus 1. FIGS. 4A and 4B show only the sensing components of the apparatus 1. It is to be appreciated that the apparatus 1 may also comprise electronic circuitry 21 which may be arranged as described above.

FIG. 4A shows a cross section of the apparatus 1, FIG. 4B shows a plan view of some of the components of the apparatus 1.

As shown in the cross section of FIG. 4A the apparatus 1 comprises a first insulating layer 31, a conductive shield 5, an electrode 3, a second insulating layer 33 and a conductive guard 35. In the examples of FIGS. 4A and 4B the conductive shield 5 and the electrode 3 are provided within the same layer of the apparatus 1.

In the examples of FIGS. 4A and 4B the first insulating layer 31 is positioned overlaying both the conductive shield 5 and the electrode 3. The first insulating layer 31 may be positioned within the apparatus 1 so that in user the first insulating layer 31 may be positioned adjacent to the user's body. In such examples the first insulating layer 31 may provide the outer surface of the apparatus 1 so that the first insulating layer 31 directly touches the user when the apparatus 1 is in use. The insulating material could comprise any suitable material. In some examples the insulating material may comprise a fabric. The fabric could comprise a material which, like human skin, has a tendency to charge positively such as nylon. In other examples the insulating material could comprise a solder mask.

In some examples the first insulating layer 31 might not be provided. In such examples the conductive shield 5 may provide, at least part, of the outer surface of the apparatus 1. In some examples the first insulating layer 31 might cover the entire of the conductive shield 5 and the electrode 3. In other examples the first insulating layer 31 may partially cover the conductive shield 5 and the electrode 3. For instance, the first insulating layer 31 could cover the electrode 3 but may leave the conductive shield 5 uncovered.

The conductive shield 5 and the electrode 3 are provided in the same layer. In the example of FIGS. 4A and 4B the conductive shield 5 and the electrode 3 are provided directly underneath the first insulating layer 31. FIG. 4B shows a plan view of the conductive shield 5 and the electrode 3. In this example the conductive shield 5 and the electrode 3 have interdigitated structures. The interdigitated structures comprise a plurality of extended projections 41, 43. The conductive shield 5 and the electrode 3 are arranged so that the extended projections 43 of the conductive shield 5 are positioned between the extended projections 41 of the electrode 3. The extended projections 43 of the conductive shield 5 are separate from the extended projections 41 of the electrode 3 so that there is no direct current path between the conductive shield 5 and the electrode 3.

The second insulating layer 33 is positioned beneath the electrode 3 and the conductive shield 5. The second insulating layer 33 may comprise a thin film of any suitable insulating material. The insulating material may comprise any material that prevents direct charge transfer between the electrode 3, the conductive shield 5 and the conductive guard 35. The second insulating layer 33 may ensure that there is no galvanic connection between the electrode 3, the conductive shield 5 and the conductive guard 35.

The conductive guard 35 comprises a conductive layer which may be arranged to protect the electrode 3 from the electronic circuitry 21 and other environmental factors. The conductive guard 35 may comprises a continuous conductive layer with no discontinuities. The conductive guard 35 may be coupled to the electronic circuitry 21. The electronic circuitry may be arranged to drive the conductive guard to the same potential as the electrode 3.

In examples of the disclosure the apparatus 1 and the plurality of sensing electrodes 3 within the apparatus 1 may be arranged to detect any suitable biosignal 9. In some examples the sensing electrodes may be arranged to detect an ECG signal. In such examples a plurality of different electrode 3 may be arranged to be coupled to different parts of the user's body. In such examples the reduction in the amount of noise which is achieved by the examples of the disclosure may remove the need for the right leg electrode in an ECG measurement. This may reduce the number of leads and simplify the process of obtaining the ECG measurements.

In the description above the term coupled means operationally coupled. Any number or combination of intervening elements can exist between coupled components, including no intervening elements.

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

I claim:

1. An apparatus comprising:
   at least one electrode, having a first potential, suitable for sensing a biosignal;
   a conductive shield provided over the at least one electrode where the conductive shield is configured to be driven to a second potential wherein the second potential is equivalent to the first potential plus a component derived from an inverted common mode voltage, wherein the common mode voltage originates from the biosignal; and
   electronic circuitry arranged to drive the conductive shield using the inverted common mode voltage;
   wherein the conductive shield is coupled to a drain to enable triboelectric charges to be dissipated.

2. An apparatus as claimed in claim 1 where the common mode voltage is an average voltage between the at least one electrode and another electrode arranged to sense the biosignal.

3. An apparatus as claimed claim 1 wherein the conductive shield is arranged to contact a user when the apparatus is in use.

4. An apparatus as claimed in claim 1 wherein the electronic circuitry comprises an amplifier having a low output impedance arranged to drive the conductive shield.

5. An apparatus as claimed in claim 4 wherein the amplifier having a low output impedance acts as the drain to enable triboelectric charges to be dissipated.

6. An apparatus as claimed in claim 1 wherein the conductive shield comprises one or more discontinuities.

7. An apparatus as claimed in claim 1 wherein the conductive shield is provided over the electrode so that in use the conductive shield is positioned between the user and the electrode.

8. An apparatus as claimed in claim 1 wherein the conductive shield and the electrode are provided in an interdigitated structure.

9. An apparatus as claimed in claim 1 comprising a plurality of electrodes and a plurality of conductive shields over the electrodes wherein each of the conductive shields are driven to a potential equivalent to the potential of the corresponding electrode plus a component derived from an inverted common mode voltage, wherein the common mode signal originates from the biosignal.

10. An apparatus as claimed in claim 9 comprising circuitry arranged to provide different input signals to the different conductive shields so that different conductive shields are driven to different potentials.

11. An apparatus as claimed in claim 1 wherein a first electrode is arranged to be coupled to a first part of a user's body and a second electrode is arranged to be coupled to a second part of a user's body.

12. An apparatus as claimed in claim 1 wherein the electrodes are capacitive electrodes arranged to detect bioelectric signals.

13. An apparatus as claimed in claim 9 comprising a conductive guard associated with the capacitive electrode wherein the conductive guard is positioned relative to the electrode to protect the electrode from the environment and the conductive guard is driven to the same potential as the capacitive electrode.

14. An apparatus as claimed in claim 9 wherein the bioelectrical signal comprises at least one of electrocardiogram signal, electroencephalogram signal, electromyogram signal, electrooculogram signal, and galvanic skin potential.

15. An apparatus comprising:
at least one electrode, having a first potential, suitable for sensing a biosignal;
a conductive shield provided over the at least one electrode where the conductive shield is configured to be driven to a second potential wherein the second potential is equivalent to the first potential plus a component derived from an inverted common mode voltage, wherein the common mode voltage originates from the biosignal; and
a plurality of electrodes and a plurality of conductive shields over the electrodes wherein each of the conductive shields are driven to a potential equivalent to the potential of the corresponding electrode plus a component derived from an inverted common mode voltage, wherein the common mode signal originates from the biosignal;
wherein the conductive shield is coupled to a drain to enable triboelectric charges to be dissipated.

16. An apparatus as claimed in claim 15, comprising circuitry arranged to provide different input signals to the different conductive shields so that different conductive shields are driven to different potentials.

17. An apparatus as claimed in claim 15, comprising a conductive guard associated with the capacitive electrode wherein the conductive guard is positioned relative to the electrode to protect the electrode from the environment and the conductive guard is driven to the same potential as the capacitive electrode.

18. An apparatus as claimed in claim 15, wherein the bioelectrical signal comprises at least one of electrocardiogram signal, electroencephalogram signal, electromyogram signal, electrooculogram signal, and galvanic skin potential.

* * * * *